United States Patent [19]
Zerbe et al.

[11] Patent Number: 5,948,430
[45] Date of Patent: Sep. 7, 1999

US005948430A

[54] WATER SOLUBLE FILM FOR ORAL ADMINISTRATION WITH INSTANT WETTABILITY

[75] Inventors: Horst Georg Zerbe, Green Pond; Jian-Hwa Guo, Sparta; Anthony Serino, Boonton, all of N.J.

[73] Assignee: LTS Lohmann Therapie-Systeme GmbH, Neuwied, Germany

[21] Appl. No.: 08/904,607

[22] Filed: Aug. 1, 1997

[30] Foreign Application Priority Data

Nov. 11, 1996 [DE] Germany ............ 196 46 392

[51] Int. Cl.⁶ ............ A61F 7/02; A61K 13/00; A61K 9/70; A61L 15/16
[52] U.S. Cl. ............ 424/435
[58] Field of Search ............ 424/435

[56] References Cited

U.S. PATENT DOCUMENTS

| | | | |
|---|---|---|---|
| 4,029,757 | 6/1977 | Mlodozeniec et al. | 424/27 |
| 4,029,758 | 6/1977 | Mlodozeniec et al. | 424/27 |
| 4,031,200 | 6/1977 | Reif | 424/27 |
| 4,876,092 | 10/1989 | Mizobuchi et al. | 424/435 |
| 4,900,552 | 2/1990 | Sanvordeker et al. | 424/435 |
| 5,047,244 | 9/1991 | Sanvordeker et al. | 424/435 |
| 5,229,164 | 7/1993 | Pins et al. | 427/3 |
| 5,346,701 | 9/1994 | Heiber et al. | 424/435 |
| 5,413,792 | 5/1995 | Ninomiya et al. | 424/435 |
| 5,472,704 | 12/1995 | Santus et al. | 424/435 |
| 5,700,478 | 12/1997 | Biegajski et al. | 424/435 |

FOREIGN PATENT DOCUMENTS

| | | |
|---|---|---|
| 1 263 312 | 11/1989 | Canada . |
| 0 219 762 | 4/1987 | European Pat. Off. . |
| 0 381 194 | 8/1990 | European Pat. Off. . |
| 0 200 508 | 10/1991 | European Pat. Off. . |
| 0 452 446 | 10/1991 | European Pat. Off. . |
| 2 449 865 | 4/1976 | Germany . |
| 3 630 603 | 3/1988 | Germany . |
| WO91/06270 | 5/1991 | WIPO . |

*Primary Examiner*—Shep K. Rose
*Attorney, Agent, or Firm*—Wenderoth, Lind & Ponack, L.L.P.

[57] ABSTRACT

A composition containing therapeutic agents and/or breath freshening agents for use in the oral cavity is disclosed. The carrier comprises water-soluble polymers in combination with certain ingredients and provides a therapeutic and/or cosmetic effect. The film is coated and dried utilizing existing coating technology and exhibits instant wettability followed by rapid dissolution/disintegration upon administration in the oral cavity.

12 Claims, No Drawings

WATER SOLUBLE FILM FOR ORAL ADMINISTRATION WITH INSTANT WETTABILITY

BACKGROUND OF THE INVENTION

A composition containing therapeutic agents and/or breath freshening agents for use in the oral cavity is disclosed. The carrier comprises water-soluble polymers in combination with certain ingredients and provides a therapeutic and/or cosmetic effect. The film is coated and dried utilizing existing coating technology and exhibits instant wettability followed by rapid dissolution/disintegration upon administration in the oral cavity.

Mucoadhesive dosage forms for application to the oral cavity which are designed to deliver therapeutic and/or cosmetic agents to the oral mucosa are known in the art. U.S. Pat. No. 5,047,244 describes a mucoadhesive carrier allowing the controlled release of a therapeutic agent via the mucosal tissue comprising an anhydrous but hydratable polymer matrix and amorphous fumed silica. An optional water-insoluble film can be added to provide a non-adhering surface. In WO 91/06270, the same authors disclose a trilaminate film suitable for prolonged delivery of an active ingredient in the oral cavity.

In a similar way, U.S. Pat. No. 4,876,092 discloses a sheet-shaped adhesive preparation comprising an adhesive layer containing certain water-soluble and water-insoluble polymers and a water-insoluble carrier which can adhere to the oral mucosa thereby releasing an active agent to the oral cavity. All the devices so far cited are not completely water soluble and will stay in the oral cavity even after the therapeutic goal has been achieved leaving the patient with a certain discomfort in the mouth resulting mainly from the support layer which leaves an insoluble residue in the mouth.

A number of attempts have been made to reduce the adverse feeling in he oral cavity caused by the rigidity and inflexibility of the support layer by introducing soft film supports. EP 0 200 508 B1 and EP 0 381 194 B1 disclose the use of polyethylene films, polyvinyl acetate, ethylene-vinyl acetate copolymers, metal foils, laminates of cloth or paper and a plastic film and similar materials as soft film supports, whereby synthetic resins like polyethylene, vinyl acetate homopolymers, and ethylene-vinyl acetate are the preferred materials. In a similar way, CA 1 263 312 discloses the use of polyolefines such as polyethylene, polypropylene, polyesters, PVC, and non-woven fabrics as soft support materials.

However, these devices still leave the patient with a considerable amount of residue from the water-insoluble support film thereby still causing a feeling of discomfort. The obvious solution to overcome tis problem was to develop mucoadhesive films which completely disintegrate, or even completely dissolve in the saliva. Fuchs and Hilmann (DE 24 49 865.5) prepared homogeneous, water-soluble films intended for buccal administration of hormones. They proposed the use of water-soluble cellulose-derivatives, like hydroxyethyl cellulose, hydroxypropyl cellulose, or methyl hydroxypropyl cellulose, as film forming agents.

Both DE 36 30 603 and EP 0 219 762 disclose the use of swellable polymers such as gelatine or corn starch as film forming agents, which upon application to the oral cavity slowly disintegrate, thereby releasing an active ingredient incorporated in the film. The same polymers can also be used to prepare films which are intended for dental cleansing, as described in EP 0 452 466 B1.

These preparations still create an adverse feeling in the mouth which is mainly caused by their initial rigidity and delayed softening. Thus, there has still been a demand for a composition for use in the oral cavity which meets the requirement of providing a pleasant feeling in the mouth. The present invention discloses methods and compositions that are capable of avoiding an adverse feeling by providing the film which is intended for application to the oral mucosa with instant wettability, while achieving adequate tensile strength in the free film to allow for easy coating, converting, and packaging of a consumer-friendly product.

DESCRIPTION OF THE INVENTION

The present invention contemplates a rapidly dissolving film which can be adhered to the oral cavity thereby releasing a pharmaceutically or cosmetically active agent, said film comprising water-soluble polymers, one or more polyalcohols, and one or ore pharmaceutically or cosmetically active ingredients. Optionally, he formulation may contain a combination of certain plasticizers or surfactants, colorants, sweetening agent, flavors, flavor enhancers, or other excipients commonly used to modify the taste of formulations intended for application to the oral cavity. The resulting film is characterized by an instant wettability which causes the film to soften immediately after application to the mucosal tissue thus preventing the patient from experiencing any prolonged adverse feeling in the mouth, and a tensile strength suitable for normal coating, cutting, slitting, and packaging operations.

The mucoadhesive film of the present invention contains as essential components a water-soluble polymer or a combination of water-soluble polymers, one or more plasticizers or surfactants, one or more polyalcohols, and a pharmaceutically or cosmetically active ingredient.

The polymers used for the mucoadhesive film include polymers which are hydrophilic and/or water-dispersible. Preferred polymers are water-soluble cellulose-derivatives. Hydroxypropylmethyl cellulose, hydroxyethyl cellulose, or hydroxypropyl cellulose, either alone, or mixtures thereof, are particularly preferred. Other optional polymers, without limiting the invention, include polyvinyl pyrrolidone, carboxymethyl cellulose, polyvinyl alcohol, sodium alginate, polyethylene glycol, natural gums like xanthane gum, tragacantha, guar gum, acacia gum, arabic gum, water-dispersible polyacrylates like polyacrylic acid, methylmethacrylate copolymer, carboxyvinyl copolymers. The concentration of the water-soluble polymer in the final film can vary between 20 and 75% (w/w), preferably between 50 and 75% (w/w).

The surfactants used for the mucoadhesive film may be one or more nonionic surfactants. When a combination of surfactants is used, the first component may be a polyoxyethylene sorbitan fatty acid ester or a α-hydro-ω-hydroxypoly (oxyethylene)poly(oxypropylene)poly (oxyethylene) block copolymer, while the second component may be a polyoxyethylene alkyl ether or a polyoxyethylene castor oil derivative. Preferably the HLB value of the polyoxyethylene sorbitan fatty acid ester should be between 10 and 20, whereby a range of 13 to 17 is particularly preferred. The α-hydro-ω-hydroxypoly (oxyethylene)poly(oxypropylene) poly(oxyethylene) block copolymer should contain at lest 35 oxypropylene-units, preferably not less than 50 oxyproplene-units.

The polyoxyethylene alkyl ether should have an HLB value between 10 and 20, whereby an HLB value of not less than 15 is preferred. The polyoxyethylene castor oil derivative has to have an HLB value of 14–16. In order to achieve the desired instant wettability, the ratio between the first and second component of the binary surfactant mixture should be kept within 1:10 and 1:1, more preferably between 1:5 and 1:3. The total concentration of surfactants in the final film depends on the properties of the other ingredients, but usually has to stay between 0.1 and 5% (w/w). The polyalcohol is used to achieve the desired level of softness of the film. Examples of polyalcohols include glycerol, polyethylene glycol, propylene glycol, glycerol monoesters with fatty acids or other pharmaceutically used polyalcohols. The concentration of the polyalcohol in the dry film usually ranges between 0.1 and 5% (w/w).

The film is well suited for the delivery of a wide range of pharmaceutically active ingredients via the mucous membranes of a patient particularly the buccal mucosa. Therapeutic agents which exhibit absorption problems due to solubility limitations, degradation in the gasto-intestinal tract, or extensive metabolism are particularly well suited. Without limiting the invention, examples of the therapeutic agents include hypnotics, sedatives, antiepileptics, awakening agents, psychoneurotropic agents, neuromuscular blocking agents, antispasmodic agents, antihistaminics, antiallergics, cardiotonics, antiarrhythmics diuretics, hypotensives, vasopressors, antitussive expectorants, thyroid hormones, sexual hormones, antidiabetics, antitumor agents, antibiotics and chemotherapeutics, and narcotics. The amount of drug to be incorporated into the film depends on the kind of drug and is usually between 0.01 and 20% (w/w), but it can be higher if necessary to achieve the desired effect.

Cosmetically active agents may include breath freshening compounds like menthol other flavors or fragrances commonly used for oral hygiene, and/or actives used for dental and/or oral cleansing like quarternary ammonium bases. The effect of flavors may be enhanced using flavor enhancers like tartaric acid, citric acid vanillin, or the like. Colorants which may optionally be mixed in the film must be safe in terms of toxicity and should be accepted by the Food And Drug Administration for use in cosmetics.

The mucoadhesive film according to the present invention can be prepared as follows: The polyalcohol, surfactants, plasticizers, and possible other ingredients except the water-soluble or water-dispersible polymer(s) are dissolved in a sufficient amount of a solvent which is compatible with them. Examples of compatible solvents include water, alcohols or mixtures thereof. After a clear solution has been formed, the water-dispersible polymer or mixture of water-dispersible polymers is slowly added with stirring, and heat if necessary, until a clear and homogeneous solution has been formed, followed by the addition of active ingredients and flavors. The solution is coated onto a suitable carrier material and dried to form a film. The carrier material must have a surface tension which allows the polymer solution to spread evenly across the intended coating width without soaking in to form a destructive bond between the two. Examples of suitable materials include non-siliconized polyethylene terephthalate film, non-siliconized kraft paper, polyethylene-impregnated kraft paper, or non-siliconized polyethylene film.

The coating of the solution onto the carrier material can be performed using any conventional coating equipment. A more preferred coating technique wold involve a knife-over-roll coating head.

The thickness of the resulting film depends on the concentration of solids in the coating solution and on the gap of the coating head and can vary between 5 sand 200 $\mu$m. Drying of the film is carried out in a high-temperature air-bath using a drying oven, drying tunnel, vacuum drier, or any other suitable drying equipment, which does not adversely affect the active ingredient(s) or flavor of the film. In order to reliably avoid an adverse feeling in the mouth, a dry film thickness of 70 $\mu$m should not be exceeded.

For better ease of use, the dry film can be cut into pieces of suitable size and shape and packed in to a suitable container.

The invention will now be explained more specifically with reference to the following examples, which are given for illustration of this invention and are not intended to be limiting thereof.

EXAMPLE 1

15 g of sorbitol 6 g of glycerol, 0.5 g of polysorbate 80 (Tween 80), 2 g of Brij 35, 25 g of lemon mint flavor, 3 g of aspartame, 15 g of 1-menthol, and 3 g of citric acid are stirred at 60° C. in a mixture of 250 g water and 250 g ethanol until a clear solution has been formed. To the solution, 30 g of hydroxypropylmethyl cellulose are added slowly under stirring until a clear and homogeneous solution has been formed. The resulting solution is allowed to cool to room temperature and coated onto a suitable carrier material, for example non-siliconized, polyethylene-coated kraft paper using conventional coating/drying equipment. Coating gap and web speed have to be adjustable to achieve a dry film thickness between 20 and 50 $\mu$m. The drying temperature depends on the length of the drying oven and the web speed and has to be adjusted to remove the solvents completely, or almost completely, from the film. The resulting film is peeled off the carrier web and cut into pieces of a shape and size suitable for the intended use.

EXAMPLE 2

3 g sorbitol 1.5 g Kollidon 30 (supplier: BASF), 5 g glycerol, 5 g propylene glycol, 5 g polyethylene glycol, 4 g polysorbate 80 (Tween 80), 8 g Brij 35, 12 g peppermint flavor, and 0.8 g aspartame are dissolved in a mixture containing 400 g water and 400 g ethanol at 60° C. under stirring. To the clear solution, 28 g hydroxypropylmethyl cellulose are added slowly under stirring. After the polymer is completely dissolved, the solution is cooled to room temperature and coated onto a suitable carrier web using the coating and drying conditions as described in the previous example. The dry film is again out into pieces of suitable size and shape.

EXAMPLE 3

15 g sorbitol, 22.5 g glycerol, 2.5 g propylene glycol, 2.5 g Brij 35, 2.5 g poloxamer 407, 3.5 g Cremophor RH 40 9 g herb mint flavor, and 0.5 aspartame are dissolved under stirring at 60° C. in a mixture containing 250 g water and 250 g ethanol. To the clear solution, 75 g hydroxypropyl cellulose are added slowly under continuous stirring. The clear solution is again coated and dried under the conditions as described in EXAMPLE 1 and the dry film is cut into pieces of a shape and size suitable for the intended use.

EXAMPLE 4

3.6 g Tween 80, 3.6 g glycerol, 39 g menthol, and 171 g Kollidon 30 are dissolved in a solution of 600 ml water and 2800 ml ethanol at ambient temperature with stirring. 247.5 g hydroxypropylmethyl cellulose is then added slowly and portionwise at 50–55° C. and stirred until completely dissolved. The mixture is then allowed to cool and added in succession are 90 g lemon mint flavor followed by a solution/suspension of 27.13 g aspartame, 18 g citric acid, and 0.17 g FD&C yellow #5 in 120 ml water with stirring. The clear solution is coated and dried under the conditions as described in EXAMPLE and the dry film is cut into pieces of a shape and size suitable for the intended use.

EXAMPLE 5

165.4 g Kollidon 30 are dissolved in a solution of 720 ml water and 2660 ml ethanol at ambient temperature with stirring. 220.5 g hydroxypropylmethyl cellulose is then added at 55–60° C. and stirred vigorously until clear and homogeneous. The mixture is then allowed to cool and added in succession are 78.75 g flavor followed by a mixture of 28.88 g nicotine salicylate and 31.5 g caramel liquid in 120 ml water with stirring. The clear, tan-colored solution is coated an dried under the conditions as described in EXAMPLE 1 and the dry film is cut into pieces of a shape and size suitable for the intended use so as to deliver a nicotine dose between 1–2 mg per piece.

We claim:

1. A monolayer film formed from a mucoadhesive composition which comprises at least one water-soluble polymer; at least one member selected from the group consisting of a polyalcohol, a surfactant and a plasticizer; at least one cosmetic or pharmaceutically ingredient; and a flavoring agent said film being one which rapidly softens and completely disintegrates in the oral environment and having a dry film thickness which is suitable for application into the month without causing adverse feeling the mouth.

2. A monolayer film according to claim 1 wherein the dry film thickness is about 70 µm.

3. A monolayer film according to claim 1 wherein the concentration of water-soluble polymer is between 20 and 75% (w/w), the concentration of surfactant is between 0.1 and 5% (w/w), the concentration of polyalcohol is between 0.1 and 5% (w/w) and the amount of pharmaceutically active ingredient is between 0.01 and 20% (w/w).

4. A monolayer film according to claim 1, wherein the water-soluble polymer is selected from the group consisting of hydroxypropylmethyl cellulose, hydroxyethyl cellulose, hydroxypropyl cellulose, polyvinyl pyrrolidone, carboxymethyl cellulose polyvinyl alcohol sodium alginate, polyethylene glycol, xanthane gum, tragacantha guar gum, acacia gym, arabic gum, polyacrylic acid, methylmethacrylate copolymer carboxyvinyl polymer and copolymers and mixtures thereof.

5. A monolayer film according to claim 1, wherein the concentration of the water-soluble polymer in the dry film lies between 20 and 75% (w/w).

6. A composition according to claim 1, wherein the polyalcohol is selected from the group consisting of glycerol, polyethylene glycol, propylene glycol, and glycerol monoesters with fatty acids.

7. A monolayer film according to claim 1 containing a polyalcohol and at least one surfactant.

8. A monolayer film according to claim 1, wherein the surfactant is a polyoxyethylene sorbitan fatty acid ester, a $\alpha$-hydroxy-$\omega$hydroxypoly-(oxyethylene)poly(oxypropylene)poly(oxypropylene) block copolylmer, a polyoxyethylene alkyl ether or a polyoxyethylene castor oil derivative or a mixture thereof.

9. A monolayer film according to claim 1, comprising sorbitol and/or polyvinylpyrrolidone together with water-soluble cellulose-derivative polymer.

10. A monolayer film according to claim 1, wherein the pharmaceutically active ingredient is selected from the group consisting of a hypnotic, a sedative, an antiepileptic, an awakening agent, a pyschoneurotropic agent, a neuromuscular blocking agent, an antispasmodic agent, an antihistaminic, an antiallergic, a cardiotonic, an antiarrhythmic, a diuretic, a hypotensive, a vasopressor, an antitussive expectorant, a thyroid hormone, a sexual hormone, an antidiabetic, an antitumor agent, an antibiotic, a chemotherapeutic, and a narcotic.

11. A monolayer film according to claim 1, wherein the cosmetically active agent is selected from the group consisting of a breath freshening compound, a favor or fragrance used or oral hygiene, an agent for dental and/or oral cleansing and mixtures thereof.

12. A molecular film according to claim 1 in a shape suitable for application into the mouth.

* * * * *

(12) REEXAMINATION CERTIFICATE (4745th)
United States Patent
Zerbe et al.

(10) Number: US 5,948,430 C1
(45) Certificate Issued: Mar. 4, 2003

(54) WATER SOLUBLE FILM FOR ORAL ADMINISTRATION WITH INSTANT WETTABILITY

(75) Inventors: Horst Georg Zerbe, Green Pond, NJ (US); Jian-Hwa Guo, Sparta, NJ (US); Anthony Serino, Boonton, NJ (US)

(73) Assignee: LTS Lohmann Therapie-Systeme GmbH, Neuwied (DE)

Reexamination Request:
No. 90/005,887, Dec. 11, 2000

Reexamination Certificate for:
Patent No.: 5,948,430
Issued: Sep. 7, 1999
Appl. No.: 08/904,607
Filed: Aug. 1, 1997 08/904,607

(30) Foreign Application Priority Data

Nov. 11, 1996 (DE) .......................... 196 46 392

(51) Int. Cl.[7] ............. A61F 7/02; A61K 13/00; A61K 9/70; A61L 15/16
(52) U.S. Cl. ...................................... 424/435
(58) Field of Search .......................... 424/435

(56) References Cited

U.S. PATENT DOCUMENTS

| 4,713,239 A | 12/1987 | Babaian et al. |
| 5,462,749 A | 10/1995 | Rencher et al. |

FOREIGN PATENT DOCUMENTS

| DE | 243925 | 11/1985 |
| EP | 0 250 187 B1 | 12/1987 |
| EP | 0 259 749 B1 | 3/1988 |
| EP | 0 781 550 A1 | 7/1997 |
| JP | 61-30516 | 2/1986 |
| JP | 5-41602 | 6/1993 |
| JP | 5-236885 | 9/1993 |
| WO | WO 91/05540 | 5/1991 |
| WO | WO 92/15289 | 9/1992 |

OTHER PUBLICATIONS

Hagers Handbuch der Pharmazeutischen Praxis, F.V. Bruchhausen (publisher), vol. 2, p. 849, Springer–Verlag, Berlin (1991) (English translation).

Drug Delivery Systems, V.V. Ranade and M.A. Hollinger (eds.), 62–66, CRC Press, Boca Raton, Fla (1996).

C.D. Ebert et al., Journal of Controlled Release, vol. 28, p. 37–44 (1994).

Database CA PLUS on STN, AN 1996:193234, abstract of JP–61–030516 (1986).

Patent Abstracts of Japan, abstract of JP 61–030516 (1986).

Y.W. Chien, Novel Drug Delivery Systems, Second Edition, p. 171–173, Marcel Dekker Inc., New York (1992).

*Primary Examiner*—Frederick Krass

(57) ABSTRACT

A composition containing therapeutic agents and/or breath freshening agents for use in the oral cavity is disclosed. The carrier comprises water-soluble polymers in combination with certain ingredients and provides a therapeutic and/or cosmetic effect. The film is coated and dried utilizing existing coating technology and exhibits instant wettability followed by rapid dissolution/disintegration upon administration in the oral cavity.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 7 and 10 is confirmed.

Claim 1 is cancelled.

Claims 2, 4–6, 8–9, and 11–12 are determined to be patentable as amended.

New claims 13–16 are added and determined to be patentable.

2. A monolayer film according to claim [1] *13*, wherein the dry film thickness is about 70 μm.

4. A monolayer film according to claim [1] *13*, wherein the water-soluble polymer is selected from the group consisting of hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthane gum, tragacantha guar gum, acacia [gym] *gum*, arabic gum, polyacrylic acid, methylmethacrylate copolymer carboxyvinyl polymer and copolymers and mixtures thereof.

5. A monolayer film according to claim [1] *13*, wherein the concentration of the water-soluble polymer in the dry film lies between 20 and 75% (w/w).

6. A [composition] *monolayer* film according to claim [1] *13*, wherein the polyalcohol is selected from the group consisting of glycerol, polyethylene glycol, propylene glycol, and glycerol monoesters with fatty acids.

8. A monolayer film according to claim [1] *13*, wherein the surfactant is a polyoxyethylene sorbitan fatty acid ester, a [α-hydroxy-ωhydroxypoly-(oxyethylene)poly(oxypropylene)poly(oxypropylene)] *α-hydroxy-ω-hydroxypoly-(oxyethylene)poly(oxypropylene)poly(oxyethylene)* block copolymer, a polyoxyethylene alkyl ether or a polyoxyethylene castor oil derivative or a mixture thereof.

9. A monolayer film according to claim [1] *13*, comprising sorbitol and/or polyvinylpyrrolidone together with water-soluble cellulose-derivative polymer.

11. A monolayer film according to claim [1] *13*, wherein the cosmetically active agent is selected from the group consisting of a breath freshening compound, a favor or fragrance used [or] *for* oral hygiene, an agent for dental and/or oral cleansing and mixtures thereof.

12. A [molecular] *monolayer* film according to claim [1] *13*, in a shape suitable for application into the mouth.

*13. A monolayer film formed from a mucoadhesive composition which comprises*
  *a) at least one water-soluble polymer;*
  *b) a surfactant alone or in combination with at least one member selected from the group consisting of a polyalcohol and a plasticizer, or a polyalcohol and a plasticizer;*
  *c) at least one cosmetic or pharmaceutical ingredient; and*
  *d) a flavoring agent,*
*said film being one which rapidly softens and completely disintegrates in the oral environment and having dry film thickness which is suitable for application into the mouth without causing adverse feeling in the mouth.*

*14. A monolayer film according to claim 13, wherein the concentration of water-soluble polymer is between 20 and 75% (w/w), the concentration of surfactant is between 0.1 and 5% (w/w), the concentration of polyalcohol is between 0.1 and 5% (w/w) and the amount of pharmaceutically active ingredient is between 0.01 and 20% (w/w).*

*15. A monolayer film according to claim 13, containing a polyalcohol and at least one surfactant.*

*16. A monolayer film according to claim 13, wherein the pharmaceutically active ingredient is selected from the group consisting of a hypnotic, a sedative, an antiepileptic, an awakening agent, a pyschoneurotropic agent, a neuromuscular blocking agent, an antispasmodic agent, an antihistaminic, an antiallergic, a cardiotonic, an antiarrhythmic, a diuretic, a hypotensive, a vasopressor, an antitussive expectorant, a thyroid hormone, a sexual hormone, an antidiabetic, an antitumor agent, an antibiotic, a chemotherapeutic, and a narcotic.*

\* \* \* \* \*